(12) United States Patent
Wu

(10) Patent No.: US 6,432,997 B1
(45) Date of Patent: Aug. 13, 2002

(54) PYRAZOLE PESTICIDES

(75) Inventor: Tai-Teh Wu, Chapel Hill, NC (US)

(73) Assignee: Rhone-Poulenc, Inc., Research Triangle Park, NC (US)

( * ) Notice: Subject to any disclaimer, the term of this patent is extended or adjusted under 35 U.S.C. 154(b) by 0 days.

(21) Appl. No.: 09/404,809

(22) Filed: Sep. 24, 1999

Related U.S. Application Data

(62) Division of application No. 08/946,132, filed on Oct. 7, 1997, now Pat. No. 5,981,565.

(51) Int. Cl.$^7$ .................. A01N 43/56; C07D 231/44
(52) U.S. Cl. ..................... 514/404; 548/367.4
(58) Field of Search .............. 548/367.4; 514/404

(56) References Cited

U.S. PATENT DOCUMENTS

| | | |
|---|---|---|
| 4,918,085 A | 4/1990 | D'Silva et al. |
| 5,047,550 A | 9/1991 | D'Silva |
| 5,232,940 A | 8/1993 | Hatton et al. |

FOREIGN PATENT DOCUMENTS

| | | |
|---|---|---|
| DE | 19511269 | 10/1995 |
| EP | 0 201 852 | 11/1986 |
| EP | 0 295 117 | 12/1988 |
| EP | 0 352 944 | 1/1990 |
| EP | 0 403 300 | 12/1990 |
| EP | 0 403 309 | 12/1990 |
| EP | 0 412 849 | 2/1991 |
| EP | 0 511 845 | 11/1992 |
| EP | 0 659 745 | 6/1995 |
| EP | 0 679 650 | 11/1995 |
| EP | 0 780 378 | 6/1997 |
| WO | WO 87/03781 | 7/1987 |
| WO | WO 92/13451 | 8/1992 |
| WO | WO 93/06089 | 4/1993 |
| WO | WO 94/21606 | 9/1994 |
| WO | WO 97/22593 | 6/1997 |
| WO | WO 97/28126 | * 8/1997 |

OTHER PUBLICATIONS

English language Derwent Abstract of EP 0 649 745 (1995).
English language Derwent Abstract of EP 0 679 650 (1995).
English language Derwent Abstract of 0 201 852 (1986).
English language Derwent Abstract of DE 195 11 269 (1995).
Chemical Specialities Manufacturing Association, Blue Book, McNair–Dorland Co., NY 1954, pp. 243–244, 261.

* cited by examiner

Primary Examiner—Robert W. Ramsuer
(74) Attorney, Agent, or Firm—Finnegan, Henderson, Farabow, Garrett & Dunner, L.L.P.

(57) ABSTRACT

The invention relates to new 1-arylpyrazole hydroxylamines and hydrazines of the formula

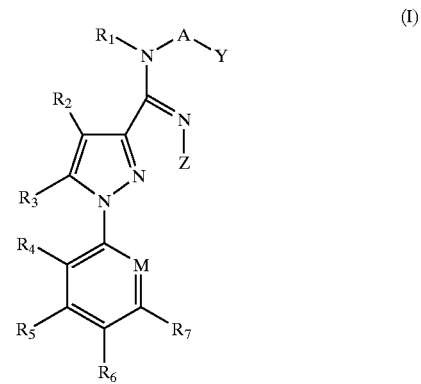

wherein the structural variables are as defined in the specification. The subject compounds are especially useful as pesticides, for controlling arthropods, especially insects, by systemic action.

15 Claims, No Drawings

PYRAZOLE PESTICIDES

This is a division of application Ser. No. 08/946,132, filed Oct. 7, 1997, now U.S. Pat. No. 5,981,565 which is incorporated herein by reference.

The present invention relates to novel 1-arylpyrazole hydroxylamines, hydrazines, and compositions containing them. The invention particularly pertains to compositions of said compounds and methods and use of said compounds for the control of arthropod, nematode, helminth or protozoan pests, in particular to the application of said compounds or compositions in agricultural methods of use, particularly as pesticides, for controlling arthropods, especially insects by systemic action.

The control of insects, nematodes or helminths by means of an active ingredient having a 1-arylpyrazole group therein has been described in such patent applications such as International Patent Publication No. WO 93/06089, WO 94/21606 and WO 87/03781 as well as in European Patent Publication Numbers 0295117, 659745, 679650, 201852 and 412849, German Patent No. DE 19511269 and U.S. Pat. No. 5,232,940.

Other compounds are disclosed in WO 92/13451, Aug. 20 1992, to Schering Agrochemicals Ltd., which describes 5-chloro-1-[2,6-dichloro-4-(trifluoromethyl)phenyl]-4-(4,5-1H-pyrazole as an intermediate, also with activity against a single species Lucilia sericata, sleep blow fly.

This Schering reference appears to be the only reference describing 1-arylpyrazole-oxime compounds as insecticides.

It is an object of the present invention to provide new pesticidal compounds of the 1-arylpyrazole family together with processes for their preparation.

A second object of the present invention is to provide pesticidal compositions and pesticidal methods of use of the pesticidal pyrazole compounds against arthropods, especially insects, plant nematodes, or helminth or protozoan pests, particularly in agricultural or horticultural crops, forestry, veterinary medicine or livestock husbandry, or in public health.

A third object of the present invention is to provide very active compounds, with broad spectrum pesticidal activity, as well as compounds with selective special activity, e.g., aphicidal, miticidal, foliar insecticidal, soil insecticidal and nematicidal, systemic, antifeeding or pesticidal activity via seed treatment.

A fourth object of the present invention is to provide compounds with substantially enhanced and more rapid activity, especially against insects and more particularly insects in their larval stages.

A fifth object of the present invention is to provide compounds with greatly improved (greater and faster) penetration into pest species when topically applied and thus provide enhanced movement of the compounds to the pesticidal site(s) of action within the pest.

Another object of the present invention is to provide compounds with high activity and improved safety to the user and the environment.

These and other objects of the invention shall become readily apparent from the detailed description of the present invention.

These objects are met in whole or in part by the instant invention.

The present invention provides arylpyrazoles of formula (I):

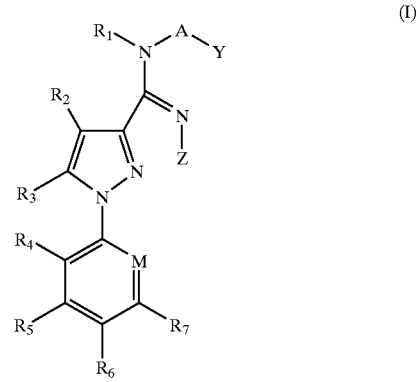

wherein:
A is —O— or —NR$_8$;
Y is hydrogen, substituted or unsubstituted alkyl, substituted or unsubstituted alkenyl, substituted or unsubstituted alkynyl, substituted or unsubstituted aryl, —S(O)$_m$R$_{10}$, —P(O)R$_{11}$R$_{12}$, —P(S)R$_{12}$, —Si(R$_{13}$)(R$_{14}$)(R$_{15}$), —C(O)R$_9$, —C(S)R$_9$, cyano or nitro;
R$_1$ is substituted or unsubstituted alkyl or substituted or unsubstituted aryl;
R$_2$ is —S(O)$_n$R$_{16}$ or alkyl or haloalkyl;
R$_3$ is hydrogen, halogen, —C(O)R$_{17}$, —S(O)$_p$R$_{18}$, alkyl, haloalkyl, —OR$_{19}$, —N=C(R$_{20}$)(R$_{21}$),alkenyl, —NR$_{22}$R$_{23}$, 1H-pyrrol-1-yl, 1H-pyrazol-1-yl, or —CH=NOH;
R$_4$, R$_5$ and R$_7$ are independently selected from hydrogen, halogen or alkyl;
R$_6$ is halogen, haloalkyl, haloalkoxy, —S(O)$_q$R$_{24}$ or SF$_5$;
R$_8$ is hydrogen or substituted or unsubstituted alkyl;
R$_9$ is hydrogen, substituted or unsubstituted alkyl of C$_1$ to C$_{20}$, substituted or unsubstituted aryl, —OR$_{25}$, —NR$_{26}$R$_{27}$, or and —SR$_{28}$;
R$_{10}$ is substituted or unsubstituted alkyl or substituted or unsubstituted aryl;
R$_{11}$ and R$_{12}$ are independently selected from alkoxy and thioalkoxy;
R$_{13}$, R$_{14}$ and R$_{15}$ are independently selected from alkyl, haloalkyl and aryl;
R$_{16}$ is alkyl, alkenyl, alkynyl, or C$_3$–C$_6$ cycloalkyl each of which is optionally substituted by one or more halogen;
R$_{17}$ is hydrogen, alkyl, alkoxy or thioalkoxy;
R$_{18}$ is alkyl, haloalkyl or aryl;
R$_{19}$ and R$_{20}$ are independently selected from hydrogen, alkyl and haloalkyl;
R$_{21}$ is alkyl, alkoxy or phenyl each of which is optionally substituted by one or more groups selected from hydroxy, halogen, alkoxy, —CN, alkyl, —S(O)$_s$-alkyl;
R$_{22}$ and R$_{23}$ are independently selected from hydrogen, NH$_2$, —S(O)$_r$R$_{29}$, —C(O)R$_{30}$, substituted or unsubstituted alkyl, substituted or unsubstituted alkenyl and alkynyl; or R$_{22}$ and R$_{23}$ may form together a divalent alkylene radical which may be interrupted by one or more heteroatoms, preferably selected from oxygen, nitrogen and sulfur;
R$_{24}$ is haloalkyl;
R$_{25}$ and R$_{28}$ are independently selected from substituted or unsubstituted alkyl and substituted and unsubstituted aryl;

$R_{26}$ and $R_{27}$ are independently selected from hydrogen, substituted or unsubstituted alkyl and substituted or unsubstituted aryl; $R_{26}$ and $R_{27}$ may form together a divalent alkylene radical which may be interrupted by one or more heteroatoms preferably selected from oxygen, nitrogen and sulfur;

$R_{29}$ is substituted or unsubstituted alkyl;

$R_{30}$ is hydrogen, alkyl, haloalkyl, aryl, alkenyl, —$OR_{31}$, —$SR_{31}$, or —$NR_{32}R_{33}$;

$R_{31}$ is alkyl or haloalkyl;

$R_{32}$ and $R_{33}$ are independently selected from hydrogen, alkyl, haloalkyl and aryl;

Z is hydrogen, substituted or unsubstituted alkyl, —$S(O)_tR_{34}$, —$C(O)R_{35}$, —$P(O)R_{36}R_{37}$, —$P(S)R_{36}R_{37}$, cyano or nitro;

$R_{34}$ is substituted or unsubstituted alkyl or substituted or unsubstituted aryl;

$R_{35}$ is hydrogen, substituted or unsubstituted alkyl, substituted or unsubstituted aryl, —$OR_{38}$, —$NR_{39}R_{40}$ or —$SR_{41}$;

$R_{36}$ and $R_{37}$ are independently selected from alkoxy, haloalkoxy, thioalkoxy and haiothioalkoxy;

$R_{38}$ and $R_{41}$ are independently selected from substituted or unsubstituted alkyl, or substituted or unsubstituted aryl;

$R_{39}$ and $R_{40}$ are independently selected from hydrogen, substituted or unsubstituted alkyl and substituted or unsubstituted aryl; or $R_{39}$ and $R_{40}$ may form together a divalent alkylene radical which may be interrupted by one or more heteroatoms preferably selected from oxygen, nitrogen and sulfur;

m, n, p, q, r, s, and t independently represent zero, one or two;

M is C-halo, C—$CH_3$, C—$CH_2F$, C—$CH_2Cl$, C—$NO_2$, or N;

or a pesticidally acceptable salt thereof.

By the term "pesticidally acceptable salts" is meant salts the anions and cations of which are known and accepted in the art for the formation of pesticidally acceptable salts. Preferably such salts are water soluble. Suitable acid addition salts formed by compounds of formula (I) containing an amine group, include salts with inorganic acids for example hydrochlorides, phosphates, sulfates and nitrates, and salts with organic acids for example acetates. Suitable salts formed with bases from compounds of formula (I) include alkali metal (for example sodium or potassium) salts, ammonium salts and organic amine (for example diethanolamine or morpholine) salts.

Preferably by the term "substituted" is meant substituted by one or more of the following substituents: halogen, hydroxy, alkoxy, alkylthio, cyano, carboxy, alkyl, haloalkyl, —C(O)alkyl, —C(O)O-alkyl, —C(O)$NH_2$, —C(O)NH-alkyl, —C(O)N(alkyl)$_2$, aryl, nitro, azido, amino, alkylamino, dialkylamino, alkylsulfenyl, alkylsulfinyl, alkylsulfonyl, aryloxy, arylthio, alkylcarbonylamino, alkylcarbonyloxy, or aryloxycarbonyl.

Unless otherwise specified, alkyl groups and moieties including them have from one to six, preferably one to four, carbon atoms, alkenyl groups have from two to six, preferably two to four, carbon atoms, and alkynyl groups have from three to six, preferably three to four carbon atoms. By the term "aryl" is meant mono or polycyclic aromatic moieties including phenyl, pyridyl, pyrimidinyl and naphthyl groups. The term "halo" before the name of a radical means that this radical is partially or completely halogenated, that is to say, substituted by F, Cl, Br or I, in any combination, preferably F or Cl. The term "halogen" means F, Cl, Br or I. It shall be understood that the rings formed by the divalent alkylene radicals represented by $R_{25}$ and $R_{26}$, $R_{26}$ and $R_{27}$, or $R_{39}$ and $R_{40}$ and including the nitrogen atoms to which they are attached are generally 5, 6 and 7-membered rings.

A preferred class of arylpyrazoles of formula (I) are those with one or more of the following features wherein:

A is —O— or —$NR_8$—;

Y is H or substituted or unsubstituted alkyl;

$R_1$ is substituted or unsubstituted alkyl;

$R_2$ is $S(O)_nR_{18}$;

$R_3$ is —$NR_{25}R_{26}$;

$R_4$ is halo;

$R_5$ and $R_7$ are hydrogen;

$R_6$ is haloalkyl;

M is C-halo; or

Z is hydrogen or substituted or unsubstituted alkyl

Another preferred class of 1-arylpyrazoles of formula (I) is one wherein:

A is —O—;

Y is hydrogen;

$R_1$ is alkyl, preferably methyl;

$R_2$ is S(O)alkyl, preferably SOMe or SOEt;

$R_3$ is —$NH_2$;

$R_4$ is Cl;

$R_5$ and $R_7$ are hydrogen;

$R_6$ is $CF_3$;

M is C—Cl; and

Z is hydrogen.

Another preferred class of 1-arylpyrazoles of formula (I) is one wherein:

A is —$NR_8$—;

Y is hydrogen;

$R_1$ is alkyl, preferably methyl;

$R_2$ is S(O)alkyl, preferably SOMe or SOEt;

$R_3$ is —$NH_2$;

$R_4$ is —Cl;

$R_5$ and $R_7$ are hydrogen;

$R_6$ is $CF_3$;

M is C—Cl; and

Z is hydrogen.

Preferred aryl groups comprising the $R_4$ to $R_7$ and M radicals in formula (I) are: 2,6-dichloro-4-trifluoromethylphenyl; 2,6-dichloro-4-trifluoromethoxyphenyl; 2-bromo-6-chloro-4-trifluoromethylphenyl; 2-bromo-6-chloro-4-trifluoromethoxyphenyl; 2,6-difluoro-4-trifluoromethylphenyl;2-chloro-4-trifluoromethylphenyl; 3-chloro-5-trifluoromethyl-2-pyridinyl; 3-chloro-5-trifluoromethoxy-2-pyridinyl; 2-bromo-6-fluoro-4-difluoromethylphenyl; 2-chloro-6-fluoro-4-trifluoromethylphenyl; 2,6-dibromo-4-trifluoromethylphenyl; 2,6-dibromo-4-trifluoromethoxyphenyl; and 2,6-dichloro-4-pentafluorothiophenyl.

Specifically preferred compounds according to the invention are:

1) 5-Amino-1-[2,6-dichloro-4-(trifluoromethyl)phenyl]-4-methylsulfinyl-N-hydroxy-N-methyl-1H-pyrazole carboximidamide (mp about 190° C.)

2) 5-Amino-1-[2,6-dichloro-4-(trifluoromethyl)phenyl]-4-trifluoromethylsulfinyl-N-hydroxy-N-methyl-1H-pyrazole carboximidamide (mp about 156° C.).

According to a further feature of the invention, compounds of general formula (I) are prepared by reacting, compounds of formula (II):

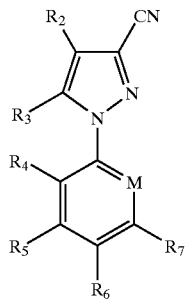

(II)

with a compound of formula (III):

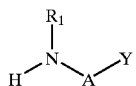

(III)

in which Y and A are defined above. The reaction is generally performed using an acid salt of a compound of formula (III), for example the hydrochloride salt, and in the presence of a base for example pyridine or an alkali metal carbonate (such as sodium carbonate) or an alkali metal acetate (such as sodium acetate) or ammonium acetate in a solvent such as methanol and/or water at a temperature from 0° C. to 100° C.

According to a further feature of the present invention compounds of general formula (I) wherein Z is H may be prepared by the reaction of a compound of formula (IV):

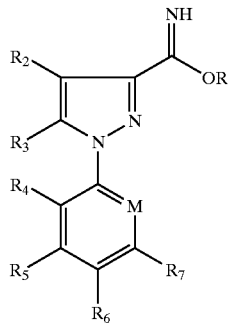

(IV)

wherein R represents alkyl with a compound of formula (III). The reaction is generally performed using an acid salt of a compound of formula (III), for example the hydrochloride salt, and optionally in the presence of a base (for example pyridine or an alkali metal carbonate such as sodium carbonate) or an alkali metal acetate (such as sodium acetate or ammonium acetate) in a solvent such as methanol and/or water and generally at a temperature from 0° C. to 100° C.

According to a further feature of the invention, compounds of formula (I) wherein Y is —S(O)$_m$R$_{10}$, —P(O)R$_{11}$R$_{12}$, —P(S)R$_{11}$R$_{12}$, —Si(R$_{13}$)(R$_{14}$)(R$_{15}$), —C(O)R$_9$, —C(S)R$_9$, cyano or nitro may be prepared by reaction of a compound of formula (I) wherein Y is hydrogen, with sulfenylating, sulfinylating, sulfonating phosphorylating, thiophosphorylating, silylating, acylating or thioacylating, cyanating, or nitrating reagent, respectively, generally in the presence of bas such as triethylamine or sodium carbonate and generally in a solvent at a temperature generally in the range –100 to 100° C.

According to a further feature of the invention, compounds of formula (I) wherein Z is substituted or unsubstituted alkyl, —S(O)tR34, —C(O)R35, —P(O)R36R37, —P(S)R36R37, cyano or nitro may be prepared by:

a) reaction of a compound of formula (IV) with alkylating, sulfenylating, sulfinylating, sulfonating, phosphorylating, thiophosphonylating, acylating, cyanating or nitrating reagent, respectively, generally in the presence of a base such as triethylamine or sodium carbonate and generally in a solvent at a temperature generally in the range from –100 to 100° C.; and b) reaction with a compound of formula (III).

The compounds of formula (II) wherein R$_2$, R$_3$, R$_4$, R$_5$, R$_6$ and M are the above described substituents can be prepared by methods described in one or more of the following: WO 94/21606, WO 93/06089, WO 87/03781, WO 97/22593; European Patent Publications EP 0295117, EP 0511845, EP 0403309, EP 0403300, EP 352944, EP 780378; U.S. Pat. Nos. 5,232,940, 5,047,550, 4,918,085; German Patent Publication No. 19511269; or by methods known to the skilled in the art.

The synthesis of higher oxidation states of the compounds of formula (I), i.e., compounds in which m, n, p, q, r, and s are 1 or 2, can be achieved by oxidation of the corresponding compounds in which those variables are 0 or 1.

Intermediates of formula (II) may be prepared by known methods (see for example the above listed references).

Certain compounds of formula (II) are novel and as such constitute a further feature of the invention.

Intermediates of formula (IV) wherein R represents alkyl may be prepared by the reaction of compounds of formula (II) with an alcohol of formula ROH where R is alkyl. The alcohol is usually employed in excess as the solvent but a co-solvent such as tetrahydrofuran may be present. The reaction is generally carried out in the presence of a base such as sodium alkoxide at a temperature of from 0° C. to 100° C.

Compounds of formula (IV) are novel and as such constitute a further feature of the invention.

Intermediates of formula (III) are known or may be prepared by known methods.

The following Example illustrates detailed methods of synthesis and their physical properties of representative pesticidal compounds of formula (I) according to the invention.

EXAMPLE 1

A mixture of 5-amino-3-cyano 1-[2,6-dichloro-4-(trifluoromethyl)phenyl]-4-methylsulfinyl-1H-pyrazole (1 g), methylhydroxylamine hydrochloride (0.26 g) and triethylamine (0.4 g) was stirred in methanol at ambient temperature for 2 hours, evaporated, washed (water) extracted with ethyl acetate to give 5-amino-1-[2,6-dichloro-4-(trifluoromethyl)phenyl]-4-methylsulfinyl-1H-pyrazole-3-carboxaldehyde oxime (0.35 g) as a white solid m.p. about 190° C. Compound 2 was prepared in a similar manner from fipronil.

Miticide, Insecticide, Aphicide, and Nematicide Use

The following representative test procedures, using compounds of the invention, were conducted to determine the pesticidal use and activity of compounds of the invention against: mites; certain insects, including aphids, two species of caterpillar, a fly, and three species of beetle larvae (one foliar feeding and two root feeding); and nematodes. The specific species tested were as follows:

| GENUS, SPECIES | COMMON NAME | (ABBREVI-) ATION) |
|---|---|---|
| Tetranychus urticae | twospotted spider mite | TSM |
| Aphis nasturtii | buckthorn aphid | BA |
| Spodoptera eridania | southern armyworm | SAW |
| Epilachna varivestis | Mexican bean beetle | MBB |
| Musca domestica | housefly | HF |
| Diabrotica u. howardi | southern corn rootworm | SCRW |
| Diabrotica virgifera | western corn rootworm | WCRW |
| Meloidogyne incognita | southern root-knot nematode | SRKN |
| Aphis gossypii | cotton aphid | CA |
| Schizaphis graminum | greenbug (aphid) | GB |
| Heliothis virescens | tobacco budworm | TBW |

Formulations

The test compounds were formulated for use according to the following methods used for each of the test procedures.

For mite, aphid, southern armyworm, Mexican bean beetle, and tobacco budworm tests, a solution or suspension was prepared by adding 10 mg of the test compound to a solution of 160 mg of dimethylformamide, 838 mg of acetone, 2 mg of a 3:1 ratio of Triton X-172: Triton X-152 (respectively, mainly anionic and nonionic low foam emulsifiers which are each anhydrous blends of alkylaryl polyether alcohols with organic sulfonates), and 98.99 g of water. The result was a concentration of 100 ppm of the test compound.

For housefly tests, the formulation was initially prepared in a similar manner to the above, but in 16.3 g of water with corresponding adjustment of other components, providing a 200 ppm concentration. Final dilution with an equal volume of a 20% by weight aqueous solution of sucrose provided a 100 ppm concentration of the test compound. When necessary, sonication was provided to insure complete dispersion.

For southern and western corn rootworm tests, a solution or suspension was prepared in the same manner as that used for the initial 200 ppm concentration for housefly. Aliquots of this 200 ppm formulation were then used by dilution with water according to the required test concentration.

For southern root-knot nematode and systemic tests for southern armyworm, cotton aphid, tobacco budworm and greenbug, a stock solution or suspension was prepared by adding 15 mg of the test compound to 250 mg of dimethylformamide, 1250 mg of acetone and 3 mg of the emulsifier blend referenced above. Water was then added to provide a test compound concentration of 150 ppm. When necessary, sonication was provided to insure complete dispersion.

For tobacco budworm contact tests, a stock solution was prepared by dissolving the compound in acetone and then further diluted to provide the required serial dilution concentrations.

Test Procedures

The above formulated test compounds were then evaluated for their pesticidal activity at the specified concentrations, in ppm (parts per million) by weight, according to the following test procedures:

Twospotted spider mite: Leaves infested with adult and nymphal stages of the two-spotted spider mite, obtained from a stock culture were placed on the primary leaves of two bean plants growing in a 6 cm. peat pot. A sufficient number of mites (150–200) for testing were transferred to the fresh plants within a period of twenty-four hours. The potted plants (one pot per compound) were placed on a revolving turntable and sprayed, sufficient to wet the plants to runoff, with 100 ml of the 100 ppm test compound formulation by use of a DeVilbiss spray gun set at 40psig. air pressure. As an untreated control, 100 ml of the water-acetone-DMF-emulsifier solution, containing no test compound, were also sprayed on infested plants. A treated control with a commercial technical compound, either dicofol or hexythiazox, formulated in the same manner, was tested as a standard. The sprayed plants were held for six days, after which a mortality count of motile forms was made.

Twospotted spider mite (ovicide test): Eggs were obtained from adults of the twospotted spider mite from a stock culture. Heavily infested leaves from the stock culture were placed on uninfested bean plants. Females were allowed to oviposit for a period of about 24 hours, after which the leaves of the plant were dipped into a solution of TEPP (tetraethyl diphosphate) in order to kill the motile forms and prevent additional egg laying. This dipping procedure, which was repeated after the plants dried, did not affect the viability of the eggs. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-emulsifier solution, containing no test compound, were also sprayed on infested plants. A treated control with a commercial technical compound, typically demeton, formulated in the same manner, was tested as a standard. The sprayed plants were held for seven days, after which a mortality count of egg forms was made along with notations on residual activity on hatched larvae.

Buckthorn or cotton aphid: Adult and nymphal stages of buckthorn or cotton aphid were reared on potted dwarf nasturtium or cotton plants, respectively. The potted plants (one pot per compound tested) infested with 100–150 aphids, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on infested plants. A treated control with a commercial technical compound, malathion or cyhalothrin, formulated in the same manner, was tested as a standard. After spraying, the pots were stored for one day on buckthorn aphid or three days for cotton aphid, after which the dead aphids were counted.

Southern armyworm: Potted bean plants, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar southern armyworm larvae were introduced into each cup which was closed and held for five days. Larvae which were unable to move the length of the body, even upon stimulation by prodding were considered dead.

Tobacco budworm: Potted cotton plants were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic dishes containing a piece of filter paper and a moistened dental wick. One randomly selected second instar tobacco budworm larva was then introduced into each cup which was closed and held for five days. Larvae unable to move the length of their body, even upon stimulation by prodding, were considered dead.

Mexican bean beetle: Potted bean plants were placed on a revolving turntable and sprayed with 100 ml of the 100 ppm test compound formulation, sufficient to wet the plants to runoff, by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar Mexican bean beetle larvae were introduced into each cup which was closed and held for five days. Larvae which were unable to move the length of the body, even upon stimulation by prodding, were considered dead.

House fly: Four to six day old adult house flies were reared according to the specifications of the Chemical Specialties Manufacturing Association (Blue Book, McNair-Dorland Co., N.Y. 1954; pages 243–244, 261) under controlled conditions. The flies were immobilized by anesthetizing with carbon dioxide and twenty five immobilized individuals, males and females, were transferred to a cage consisting of a standard food strainer and a wrapping-paper-covered surface. Ten ml of the 100 ppm test compound formulation were added to a souffle cup containing an absorbent cotton pad. As an untreated control, 10 ml of a water-acetone-DMF-emulsifier-sucrose solution, containing no test compound, were applied in a similar manner. A treated control with a commercial technical compound, malathion, formulated in the same manner, was tested as a standard. The bait cup was introduced inside the food strainer prior to admitting the anesthetized flies. After 24 hours, flies which showed no sign of movement on stimulation were considered dead.

Southern or western corn rootworm: Into a jar containing 60 g of sandy loam soil was added 1.5 ml of an aqueous formulation consisting of an aliquot of the 200 ppm test compound formulation, diluted with water as appropriate for the final soil concentration of the test compound, 3.2 ml of water and five pregerminated corn seedlings. The jar was shaken thoroughly to obtain an even distribution of the test formulation. Following this, twenty corn rootworm eggs (or optionally ten first instar larvae in the case of WCRW) were placed into a cavity, which was made in the soil. Vermiculite (1 ml), used optionally in the case of WCRW tests, and water (1.7 ml) were then added to this cavity. In a similar manner, an untreated control was prepared by application of the same size aliquot of a water-acetone-DMF-emulsifier solution, containing no test compound. Additionally, a treated control with a commercial technical compound (selected typically from terbufos, fonofos, phorate, chlorpyrifos, carbofuran, isazophos, or ethoprop), formulated in the same manner was used as needed as a test standard. After 7 days, the living rootworm larvae were counted using a well known "Berlese" funnel extraction method.

Southern root-knot nematode: Infected roots of tomato plants, containing egg masses of southern root-knot nematode, were removed from a stock culture and cleaned of soil by shaking and washing with tap water. The nematode eggs were separated from the root tissue and rinsed with water. Samples of the egg suspension were placed on a fine screen over a receiving bowl, in which the water level was adjusted to be in contact with the screen. From the bowl, juveniles were collected on a fine screen. The bottom of a cone-shaped container was plugged with coarse vermiculite and then filled to within 1.5 cm of the top with about a 200 ml volume of pasteurized soil. Then into a hole made in the center of the soil in the cone was pipetted an aliquot of the 150 ppm test compound formulation. A treated control with a commercial technical compound, fenamifos, formulated in a similar manner, was tested as a standard. As an untreated control, an aliquot of a water-acetone-DMF-emulsifier solution, containing no test compound, was applied in a similar manner. Immediately after treatment of the soil with the test compound there were added to the top of each cone 1000 second stage juvenile southern root-knot nematodes. After 3 days, a single healthy tomato seedling was then transplanted into the cone. The cone, containing the infested soil and tomato seedling, was kept in the greenhouse for 3 weeks. At the termination of the test, roots of the tomato seedling were removed from the cone and evaluated for galling on a rating scale relative to the untreated control as follows:

| | |
|---|---|
| 1- | severe galling, equal to untreated control |
| 3- | light galling |
| 4- | very light galling |
| 5- | no galling, ie, complete control |

These results were then converted to an $ED_3$ or $ED_5$ value (effective dose to provide a 3 or 5 gall rating).

Southern armyworm on tomato—systemic evaluation: This test was conducted in conjunction with the southern root-knot nematode evaluation (discussed below). The tomato plants, grown in the soil (at an initial compound test screening rate of 6.6 ppm soil concentration or about 150 ppm solution concentration) for nematode evaluation, were then utilized for evaluation of a compound's uptake via roots and subsequent systemic transport to the tomato foliage. At the termination of the nematode test, 21 days after treatment, the tomato foliage was excised, placed into a plastic container, and infested with second instar larvae of southern armyworm. After about 5 days, the larvae were examined for percent mortality.

Cotton aphid and tobacco budworm (on cotton) and greenbug and tobacco budworm (on sorghum)—systemic evaluation: A 7.0 ml aliquot of the 150 ppm nematode test solution was applied to deliver the equivalent of 10.0 ppm soil concentration dose as a drench to 6 cm pots containing cotton and sorghum plants. The cotton plants were previously infested with cotton aphids about two days before treatment and greenbug one day before treatment. After holding the plants about three days, the plants were rated for aphid activity. Again at six days, the plants were rated for aphid activity and the cotton aphids and greenbugs were counted and mortality was assessed. Portions of the cotton and sorghum foliage were excised, placed in separate plastic containers, and infested with second instar larvae of tobacco budworm. The potted plants were dipped in sulfotepp to kill the remaining aphids and returned to the greenhouse for regrowth. Thirteen days after treatment, the remaining foliage was excised and fed to tobacco budworms. Mortality was assessed six days after infestation.

Cotton aphid and southern armyworm (on cotton) and greenbug and southern armyworm (on sorghum)—systemic evaluation: A stock solution or suspension was prepared to deliver 5 ml of a 20 ppm soil concentration dose (and subsequent dilutions) as a drench to 6 cm pots containing cotton and sorghum plants. The cotton plants were previously infested with cotton aphids about two days before treatment and greenbug one day before treatment. After holding the plants about three days, the plants were rated for aphid activity. Again at six days, the plants were rated for aphid activity and the cotton aphids and greenbugs were counted and mortality was assessed. Portions of the cotton and sorghum foliage were excised, placed in separate plastic containers, and infested with second instar larvae of southern armyworms. The potted plants were dipped in sulfotepp to kill the remaining aphids and returned to the greenhouse for regrowth. Thirteen days after treatment the remaining foliage was excised and fed to southern armyworm. Mortality was assessed six days after infestation.

Cotton aphid and southern armyworm (on cotton and oats)—seed treatment evaluation: Technical material was applied to the seed of oats and cotton by placing the compound and the seed in an appropriate sized jar and rolling the jar on a ball mill. Assay of the material applied to the seed was by weight. Seed was then planted. When germinated and emerged, the plants were infested at the appropriate intervals with host insects. Mortality was assessed on those insects.

Tobacco budworm—contact evaluation: The following topical application method provides an assessment of contact toxicity of a compound to tobacco budworm larvae. The test compound solution at sequential two-fold dilution concentrations from 10 down to 0.16 $\mu g/\mu l$ was applied by a microinjector in replicated 1 $\mu l$ portions to the dorsum of approximately 20 mg tobacco budworm larvae. This is equivalent to applied doses of 500 down to 8 $\mu g/g$ body weight. An acetone treated control, without any test compounds, was also applied. A treated control with a commercial technical compound, cypermethrin or thiodicarb, also in acetone was used as a standard. The treated larvae were placed, individually, in separate plastic petri dishes containing an untreated cotton leaf and a moist dental wick. The treated larvae were maintained at about 27° C. and 50% relative humidity. The percent mortality was rated 1 and 4 days after treatment.

Compound Numbers 1 and 2 of the invention showed insecticidal activity in one or more of the above evaluation methods, with particularly good activity in the systemic tests.

Methods and Compositions

The present invention provides a method for the systemic control of arthropods at a locus, especially some insects or mites which feed on the above ground portions of plants. Control of such foliar pests may be provided by direct foliar application or by application for example soil spray or granule application to the plant roots or plant seeds with subsequent systemic translocation to the above ground portions of the plants. Such systemic activity includes the control of insects which reside not only at the point of application but at a remote part of the plant for example by translocation from one side of a leaf to the other or from a treated leaf to an untreated leaf. Examples of the classes of insect pests which may be systemically controlled by the arylpyrazoles of the invention include the Homoptera order (piercing-sucking), Hemiptera order (piercing-sucking), and Thysanoptera order. The invention is especially appropriate for aphids and thrips.

As is evident from the foregoing pesticidal uses, the present invention provides pesticidally active arylpyrazoles and methods of use of said arylpyrazoles for the control of a number of pest species which includes: arthropods, especially insects or mites; plant nematodes; or helminth or protozoan pests. The arylpyrazoles of formula (I) or pesticidally acceptable salts thereof thus are advantageously employed in practical uses, for example, in agricultural or horticultural crops, forestry, veterinary medicine or livestock husbandry, or in public health. From this point forward, whenever the term "arylpyrazoles of formula (I)" is used this term embraces arylpyrazoles of formula (I) and their pesticidally acceptable salts. The term "arylpyrazole of formula (I)" embraces a arylpyrazole of formula (I) and a pesticidally acceptable salt thereof.

The present invention therefore provides a method of control of pests at a locus which comprises the treatment of the locus (e.g., by application or administration) with an effective amount of a arylpyrazole of formula (I) or a pesticidally acceptable salt thereof, wherein the substituent groups are as hereinbefore defined. The locus includes, for example, the pest itself or the place (plant, animal, field, structure, premises, forest, orchard, waterway, soil, plant or animal product, or the like) where the pest resides or feeds.

The arylpyrazoles of this invention may in addition be used to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the arylpyrazoles are advantageously applied to or incorporated at an effective rate into the soil in which crops are planted or to be planted or to the seeds or growing plant roots.

In the area of public health, the arylpyrazoles are especially useful in the control of many insects, especially filth flies or other Dipteran pests, such as houseflies, stableflies, soldierflies, hornflies, deerflies, horseflies, midges, punkies, blackflies, or mosquitoes.

Arylpyrazoles of the invention may be used in the following applications and on the following pests including arthropods, especially insects or mites, nematodes, or helminth or protozoan pests:

In the protection of stored products, for example cereals, including grain or flour, groundnuts, animal feedstuffs, timber or household goods, e.g. carpets and textiles, arylpyrazoles of the invention are useful against attack by arthropods, more especially beetles, including weevils, moths or mites, for example Ephestia spp. (flour moths), Anthrenus spp. (carpet beetles), Tribolium spp. (flour beetles), Sitophilus spp. (grain weevils) or Acarus spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, Reticulitermes spp., Heterotermes spp., Coptotermes spp.

In agriculture against adults, larvae and eggs of Lepidoptera (butterflies and moths), e.g. Heliothis spp. such as

*Heliothis virescens* (tobacco budworm), *Heliothis armigera* and *Heliothis zea*. Against adults and larvae of Coleoptera (beetles) e.g. *Anthonomus* spp. e.g. *grandis* (cotton boll weevil), *Leptinotarsa decemlineata* (Colorado potato beetle), *Diabrotica* spp. (corn rootworms). Against Heteroptera (Hemiptera and Homoptera) e.g. Psylla spp., Bemisia spp., Trialeurodes spp., Aphis spp., Myzus spp., *Megoura viciae,* Phylloxera spp., Nephotettix spp. (rice leaf hoppers), Nilaparvata spp.

Against Diptera e.g. Musca spp. Against Thysanoptera such as *Thrips tabaci.* Against Orthoptera such as Locusta and Schistocerca spp., (locusts and crickets) e.g. Gryllus spp., and Acheta spp. for example, *Blatta orientalis, Periplaneta americana, Blatella germanica, Locusta migratoria migratorioides,* and *Schistocerca gregaria.* Against Collembola e.g. Periplaneta spp. and Blattela spp. (roaches). Against Isoptera e.g. Coptotermes spp. (termites).

Against arthropods of agricultural significance such as Acari (mites) e.g. Tetranychus spp., and Panonychus spp.

Against nematodes which attack plants or trees of importance to agriculture, forestry or horticulture either directly or by spreading bacterial, viral, mycoplasma or fungal diseases of the plants. For example root-knot nematodes such as Meloidogyne spp. (e.g. *M. incognita*).

In the field of veterinary medicine or livestock husbandry or in the maintenance of public health against arthropods, helminths or protozoa which are parasitic internally or externally upon vertebrates, particularly warm-blooded vertebrates, for example domestic animals, e.g. cattle, sheep, goats, equines, swine, poultry, dogs or cats, for example Acarina, including ticks (e.g. Ixodes spp., Boophilus spp. e.g. *Boophilus microplus,* Rhipicephalus spp. e.g. *Rhipicephalus appendiculatus* Ornithodorus spp. (e.g. *Ornithodorus moubata*) and mites (e.g. Damalinia spp.); Diptera (e.g. Aedes spp., Anopheles spp., Musca spp., Hypoderma spp.); Hermiptera.; Dictyoptera (e.g. Periplaneta spp., Blatella spp.); Hymenoptera; for example against infections of the gastro-intestinal tract caused by parasitic nematode worms, for example members of the family Trichostrongylidae; in the control and treatment of protozoal diseases caused by, for example, Eimeria spp. e.g. *Trypanosoms cruzi,* Leishaminia spp., Plasmodium spp., Babesis spp., Trichomonadidae spp., Toxoplasma spp. and Theileria spp.

In practical use for the control of arthropods, especially insects or mites, or nematode pests of plants, a method, for example, comprises applying to the plants or to the medium in which they grow an effective amount of a arylpyrazole of the invention. For such a method, the active arylpyrazole is generally applied to the locus in which the arthropod or nematode infestation is to be controlled at an effective rate in the range of about 5 g to about 1 kg of the active arylpyrazole per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. More preferably an effective rate range of the active arylpyrazole is from about 50 g/ha to about 400 g/ha.

When a pest is soil-borne, the active arylpyrazole generally in a formulated composition, is distributed evenly over the area to be treated (ie, for example broadcast or band treatment) in any convenient manner and is applied at rates from about 5 to about 1 kg ai/ha, preferably from about 50 to about 250 g ai/ha. When applied as a root dip to seedlings or drip irrigation to plants the liquid solution or suspension contains from about 0.075 to about 1000 mg ai/l, preferably from about 25 to about 200 mg ai. Application may be made, if desired, to the field or crop-growing area generally or in close proximity to the seed or plant to be protected from attack. The active component can be washed into the soil by spraying with water over the area or can be left to the natural action of rainfall. During or after application, the formulated arylpyrazole can, if desired, be distributed mechanically in the soil, for example by ploughing, disking, or use of drag chains. Application can be prior to planting, at planting, after planting but before sprouting has taken place, or after sprouting.

The arylpyrazoles of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or arylpyrazoleed into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the arylpyrazoles of the invention and methods of use thereof are of particular value in the control of arthropods, helminths or protozoa which are injurious to, or spread or act as vectors of diseases domestic animals, for example those hereinbefore mentioned, and more especially in the control of ticks, mites, lice, fleas, midges, or biting, nuisance or myiasis flies. The arylpyrazoles of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, arylpyrazoles of the invention may be useful for coccidiosis, a disease caused by infections from protozoan parasites of the genus Eimeria. It is an important potential cause of economic loss in domestic animals and birds, particularly those raised or kept under intensive conditions. For example, cattle, sheep, pigs or rabbits may be affected, but the disease is especially important in poultry, particularly in chickens. Administration of a small amount of a arylpyrazole of the invention, preferably by a combination with feed is effective in preventing or greatly reducing the incidence of coccidiosis. The arylpyrazoles are effective against both the cecal form and the intestinal forms. Furthermore, the arylpyrazoles of the invention may also exert an inhibiting effect on oocytes by greatly reducing the number and sporulation of those produced. The poultry disease is generally spread by the birds picking up the infectious organism in droppings in or on contaminated litter, ground, food, or drinking water. The disease is manifested by hemorrhage, accumulation of blood in the ceca, passage of blood to the droppings, weakness and digestive disturbances. The disease often terminates in the death of the animal, but the fowl which survive severe infections have had their market value subtantially reduced as a result of the infection.

The compositions hereinafter described for application to growing crops or crop growing loci or as a seed dressing may, in general, alternatively be employed for topical application to animals or in the protection of stored products, household goods, property or areas of the general environment. Suitable means of applying the arylpyrazoles of the invention include:

- to growing crops as foliar sprays, dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;
- to animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;
- to the environment in general or to specific locations where pests may lurk, including stored products, timber, household goods, or domestic or industrial premises, as sprays, fogs, dusts, smokes, wax-smears, lacquers, granules or baits,.or in tricklefeeds to waterways, wells, reservoirs or other running or standing water;
- to domestic animals in feed to control fly larvae feeding in their feces.
- In practice, the arylpyrazoles of the invention most frequently form parts of compositions. These compositions can be employed to control: arthropods, especially insects or mites; nematodes; or helminth or protozoan pests. The compositions may be of any type known in the art suitable for application to the desired pest in any premises or indoor or outdoor area or by internal or external administration to vertebrates. These compositions contain at least one arylpyrazole of formula (I) or a pesticidally acceptable salt thereof, such as described earlier, as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the arylpyrazoles employed in the invention may be combined with all the solid or liquid additives corresponding to the usual techniques of formulation.

Compositions, suitable for applications in agriculture, horticulture, or the like include formulations suitable for use as, for example, sprays, dusts, granules, fogs, foams, emulsions, or the like.

The effective use doses of the arylpyrazoles employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

The carrier may also be liquid, for example: water; alcohols, particularly: butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformarnide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above arylpyrazoles. The presence of at least one surface-active agent is generally essential when the active ingredient and/or the inert carrier are only slightly water soluble or are not water soluble and the carrier agent of the composition for application is water.

Compositions of the invention may further contain other additives such as. adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

Compositions containing arylpyrazoles of formula (I), or pesticidally acceptable salts thereof, which may be applied to control arthropod, plant. nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavouring agents, dyes, or auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active arylpyrazoles which may be included in, or used in conjunction with the compositions of the present invention are: acephate, chlorpyrifos, demeton-S-methyl, disulfoton, ethoprofos, fenitrothion, fenamiphos, fonofos, isazophos, isofenphos, malathion, monocrotophos, parathion, phorate, phosalone, pirimiphos-methyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

For their agricultural application, the arylpyrazoles of the formula (I), or pesticidally acceptable salts thereof, are therefore generally in the form of compositions, which are in various solid or liquid forms.

Solid forms of compositions which can be used are dusting powders (with a content of the arylpyrazole of formula (I), or a pesticidally acceptable salt thereof, ranging up to 80%), wettable powders or granules (including water dispersible granules), particularly those obtained by extrusion, compacting, impregnation of a granular carrier, or granulation starting from a powder (the content of the arylpyrazole of formula (I), or a pesticidally acceptable salt thereof, in these wettable powders or granules being between about 0.5 and about 80%). Solid homogenous or heterogenous compositions containing one or more arylpyrazoles of formula (I), or pesticidally acceptable salts thereof, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by arylpyrazoles of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The arylpyrazoles or compositions according to the invention are conveniently applied to vegetation and in particular to roots or leaves having pests to be eliminated. Another method of application of the arylpyrazoles or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more arylpyrazoles of formula (I), or pesticidally acceptable salts thereof, or of total active ingredients (that is to say the arylpyrazole of formula (I), or a pesticidally acceptable salt thereof, together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more arylpyrazoles of formula (I) or pesticidally acceptable salts thereof. For administration to animals orally or parenterally, including percutaneously solid or liquid compositions, these normally contain from about 0.1% to about 90% by weight of one or more arylpyrazoles of formula (I) or pesticidally acceptable salts thereof. Medicated feedstuffs normally contain from about 0.001% to about 3% by weight of one or more arylpyrazoles of formula (I) or pesticidally acceptable salts thereof. Concentrates or supplements for mixing with feedstuffs normally contain from about 5% to about 90%, preferably from about 5% to about 50%, by weight of one or more arylpyrazoles of formula (I) or pesticidally acceptable salts thereof. Mineral salt licks normally contain from about 0.1% to about 10% by weight of one or more arylpyrazoles of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more arylpyrazoles of formula (I) or pesticidally acceptable salts thereof. Suitable concentrations in treated waters are between about 0.0001 ppm and about 20 ppm, more particularly about 0.001 ppm to about 5.0 ppm. of one or more arylpyrazoles of formula (I), or pesticidally acceptable salts thereof, and may be used therapeutically in fish farming with appropriate exposure times. Edible baits may contain from about 0.01% to about 5%, preferably from about 0.01% to about 1.0%, by weight, of one or more arylpyrazoles of formula (I) or pesticidally acceptable salts thereof.

When administered to vertebrates parenterally, orally or by percutaneous or other means, the dosage of arylpyrazoles of formula (I), or pesticidally acceptable salts thereof, will depend upon the species, age, or health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 2A–2M illustrate compositions for use against arthropods, especially mites or insects, plant nematodes, or helminth or protozoan pests which comprise, as active ingredient, arylpyrazoles of formula (I), or pesticidally acceptable salts thereof, such as those described in preparative examples. The compositions described in EXAMPLES 2A–2M can each be diluted to give a sprayable composition at concentrations suitable for use in the field. Generic chemical descriptions of the ingredients (for which all of the following percentages are in weight percent), used in the composition EXAMPLES 2A–2M exemplified below, are as follows:

| Trade Name | Chemical Description |
| --- | --- |
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No 2 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 2A

A water soluble concentrate is prepared with the composition as follows:

| Active ingredient | 7% |
| --- | --- |
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 2B

An emulsifiable concentrate (EC) is prepared with the composition as follows:

| | |
|---|---|
| Active ingredient | 25% (max) |
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

EXAMPLE 2C

A wettable powder (WP) is prepared with the composition as follows:

| | |
|---|---|
| Active ingredient | 40% |
| Arylan S | 2% |
| Darvan No 2 | 5% |
| Celite PF | 53% |

The ingredients are mixed and ground in a hammer-mill to a powder with a particle size of less than 50 microns.

EXAMPLE 2D

An aqueous-flowable formulation is prepared with the composition as follows:

| | |
|---|---|
| Active ingredient | 40.00% |
| Ethylan BCP | 1.00% |
| Sopropon T360. | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

EXAMPLE 2E

An emulsifiable suspension concentrate is prepared with the composition as follows:

| | |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a beadmill until a mean particle size of less than 3 microns is obtained.

EXAMPLE 2F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 2G

A dusting powder is prepared with the composition as follows:

| | |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 2H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 2I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 2J

A wettable powder is prepared with the composition as follows:

| Active ingredient | 50% |
|---|---|
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active arylpyrazole and applied to a locus of infestation by arthropods, for example, dipterous larvae or plant nematodes, by spraying, or to domestic animals infested by, or at risk of infection by arthropods, helminths or protozoa, by spraying or dipping, or by oral administration in drinking water, to control the arthropods, helminths or protozoa.

EXAMPLE 2K

A slow release bolus composition is formed from granules containing the following components in varying percentages (similar to those described for the previous compositions) depending upon need:

Active ingredient

Density agent

Slow-release agent

Binder

The intimately mixed ingredients are formed into granules which are compressed into a bolus with a specific gravity of 2 or more. This can be administered orally to ruminant domestic animals for retention within the reticulo-rumen to give a continual slow release of active arylpyrazole over an extended period of time to control infestation of the ruminant domestic animals by arthropods, helminths or protozoa.

EXAMPLE 2L

A slow release composition in the form of granules, pellets, brickettes or the like can be prepared with compositions as follows:

| Active ingredient | 0.5 to 25% |
|---|---|
| Polyvinyl chloride | 75 to 99.5% |
| Dioctyl phthalate (plasticizer) | |

The components are blended and then formed into suitable shapes by melt-extrusion or molding. These composition are useful, for example, for addition to standing water or for fabrication into collars or eartags for attachment to domestic animals to control pests by slow release.

EXAMPLE 2M

A water dispersible granule is prepared with the composition as follows:

| Active ingredient | 85% (max) |
|---|---|
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. An arylpyrazole of formula (I):

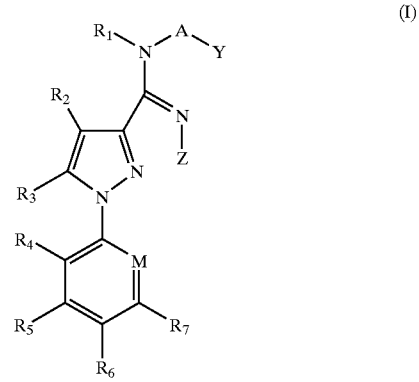

wherein:

A is —$NR_8$;

Y is hydrogen, substituted or unsubstituted alkyl, substituted or unsubstituted alkenyl, substituted or unsubstituted alkynyl, substituted or unsubstituted aryl, —$S(O)_m R_{10}$, —$P(O)R_{11}R_{12}$, —$P(S)R_{12}$, —$Si(R_{13})(R_{14})(R_{15})$, —$C(O)R_9$, —$C(S)R_9$, cyano or nitro;

$R_1$ is substituted or unsubstituted alkyl or substituted or unsubstituted aryl;

$R_2$ is —$S(O)_n R_{16}$;

$R_3$ is —$NR_{22}R_{23}$:

$R_4$, $R_5$ and $R_7$ are independently selected from hydrogen, halogen and alkyl;

$R_6$ is halogen, haloalkyl, haloalkoxy, $S(O)_q R_{24}$ or $SF_5$;

$R_8$ is hydrogen or substituted or unsubstituted alkyl;

$R_9$ is hydrogen, substituted or unsubstituted alkyl of $C_1$ to $C_{20}$, substituted or unsubstituted aryl, —$OR_{25}$, —$NR_{26}R_{27}$, or —$SR_{20}$;

$R_{10}$ is substituted or unsubstituted alkyl or substituted or unsubstituted aryl;

$R_{11}$ and $R_{12}$ are independently selected from alkoxy and thioalkoxy;

$R_{13}$, $R_{14}$ and $R_{15}$ are independently selected from alkyl, haloalkyl and aryl;

$R_{16}$ is alkyl, alkenyl, alkynyl, or $C_3$–$C_6$ cycloalkyl, each of which is substituted or unsubstituted by one or more halogen;

$R_{22}$ and $R_{23}$ are independently selected from hydrogen, $NH_2$, —$S(O)_rR_{29}$, —$C(O)R_{30}$, substituted or unsubstituted alkyl, substituted or unsubstituted alkenyl and substituted or unsubstituted alkynyl; or $R_{22}$ and $R_{23}$ may form together a divalent alkylene radical which may be interrupted by one or more heteroatoms;

$R_{24}$ is haloalkyl;

$R_{25}$ and $R_{28}$ are independently selected from substituted or unsubstituted alkyl and substituted or unsubstituted aryl;

$R_{26}$ and $R_{27}$ are independently selected from hydrogen, substituted or unsubstituted alkyl and substituted or unsubstituted aryl; or $R_{28}$ and $R_{27}$ may form together a divalent alkylene radical which may be interrupted by one or more heteroatoms;

$R_{29}$ is substituted or unsubstituted alkyl;

$R_{30}$ is hydrogen, alkyl, haloalkyl, aryl, alkenyl, —$OR_{31}$, —$SR31$, or —$NR_{32}R_{33}$;

$R_{31}$ is alkyl or haloalkyl;

$R_{32}$ and $R_{33}$ are independently selected from hydrogen, alkyl, haloalkyl and aryl;

Z is hydrogen, substituted or unsubstituted alkyl, —$S(O)_tR_{34}$, —$C(O)R_{35}$, —$P(O)R_{36}R_{37}$, —$P(S)R_{36}R_{37}$, cyano or nitro;

$R_{34}$ is substituted or unsubstituted alkyl or substituted or unsubstituted aryl;

$R_{35}$ is hydrogen, substituted or unsubstituted alkyl, substituted or unsubstituted aryl, —$OR_{38}$, —$NR_{39}R_{40}$ or —$SR_{41}$;

$R_{36}$ and $R_{37}$ are independently selected from alkoxy, haloalkoxy, thioalkoxy and halothioalkoxy;

$R_{38}$ and $R_{41}$ are independently selected from substituted or unsubstituted alkyl and substituted or unsubstituted aryl;

$R_{39}$ and $R_{40}$ are independently selected from hydrogen, substituted or unsubstituted alkyl and substituted or unsubstituted aryl; or $R_{39}$ and $R_{40}$ may form together a divalent alkylene radical which may be interrupted by one or more heteroatoms:

m, n, q, r, and t independently represent zero, one or two;

M is C-halo, C—$CH_3$, C—$CH_2F$, C—$CH_2Cl$, C—$NO_2$, or N;

or a pesticidally acceptable salt thereof.

2. An arylpyrazole according to claim 1, wherein said arylpyrazole comprises one or more of the following features:

A is —N $R_8$—;

Y is substituted or unsubstituted alkyl;

$R_1$ is substituted or unsubstituted alkyl;

$R_2$ is $S(O)_nR_{16}$;

$R_3$ is —$NR_{22}R_{23}$;

$R_4$ is halo;

$R_5$ and $R_7$ are hydrogen;

$R_6$ is haloalkyl;

M is C-halo; or

Z is hydrogen or substituted or unsubstituted alkyl.

3. An arylpyrazole according to claim 1, wherein:

A is —$NR_8$—,

Y is hydrogen;

$R_1$ is alkyl;

$R_2$ is S(O)alkyl;

$R_3$ is —$NH_2$;

$R_4$ is —Cl;

$R_5$ and $R_7$ are hydrogen;

$R_6$ is $CF_3$;

M is C—Cl; and

Z is hydrogen.

4. An arylpyrazole according to claim 3, wherein:

$R_1$ is methyl; and $R_2$ is SOMe or SOEt.

5. A pesticidal composition comprising:

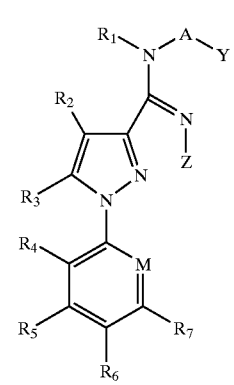

(I)

wherein:

A is —$NR_8$;

Y is hydrogen, substituted or unsubstituted alkyl, substituted or unsubstituted alkenyl, substituted or unsubstituted alkynyl, substituted or unsubstituted aryl, —$S(O)_mR_{10}$, —$P(O)R_{11}R_{12}$, —$P(S)R_{12}$, —$Si(R_{13})(R_{14})(R_{15})$, —$C(O)R_9$, —$C(S)R_9$, cyano or nitro;

$R_1$ is substituted or unsubstituted alkyl or substituted or unsubstituted aryl;

$R_2$ is —$S(O)_nR_{16}$;

$R_3$ is —$NR_{22}R_{23}$;

$R_4$, $R_5$ and $R_7$ are independently selected from hydrogen, halogen and alkyl;

$R_6$ is halogen, haloalkyl, haloalkoxy, $S(O)_qR_{24}$ or $SF_5$;

$R_8$ is hydrogen or substituted or unsubstituted alkyl;

$R_9$ is hydrogen, substituted or unsubstituted alkyl of $C_1$ to $C_{20}$, substituted or unsubstituted aryl, —$OR_{25}$, —$NR_{26}R_{27}$, or —$SR_{28}$;

$R_{10}$ is substituted or unsubstituted alkyl or substituted or unsubstituted aryl;

$R_{11}$ and $R_{12}$ are independently selected from alkoxy and thioalkoxy;

$R_{13}$, $R_{14}$ and $R_{15}$ are independently selected from alkyl, haloalkyl and aryl;

$R_{16}$ is alkyl, alkenyl, alkynyl, or $C_3$–$C_6$ cycloalkyl, each of which is substituted: or unsubstituted by one or more halogen;

$R_{22}$ and $R_{23}$ are independently selected from hydrogen, NH2, —$S(O)_rR_{29}$, —$C(O)R_{30}$, substituted or unsubstituted alkyl, substituted or unsubstituted alkenyl and substituted or unsubstituted alkynyl; or $R_{22}$ and $R_{23}$ may form together a divalent alkylene radical which may be interrupted by one or more heteroatoms;

$R_{24}$ is haloalkyl;

$R_{25}$ and $R_{28}$ are independently selected from substituted or unsubstituted alkyl and substituted or unsubstituted aryl;

$R_{26}$ and $R_{27}$ are independently selected from hydrogen, substituted or unsubstituted alkyl and substituted or unsubstituted aryl; $R_{26}$ and $R_{27}$ may form together a divalent alkylene radical which may be interrupted by one or more heteroatoms;

$R_{29}$ is substituted or unsubstituted alkyl;

$R_{30}$ is hydrogen, alkyl, haloalkyl, aryl, alkenyl, —$OR_{31}$, —$SR_{31}$, or —$NR_{32}R_{33}$;

$R_{31}$ is alkyl or haloalkyl;

$R_{32}$ and $R_{33}$ are independently selected from hydrogen, alkyl, haloalkyl and aryl;

Z is hydrogen, substituted or unsubstituted alkyl, —$S(O)_rR_{34}$, —$C(O)R_{35}$, —$P(O)R_{36}R_{37}$, —$P(S)R_{36}R_{37}$, cyano or nitro;

$R_{34}$ is substituted or unsubstituted alkyl or substituted or unsubstituted aryl;

$R_{35}$ is hydrogen, substituted or unsubstituted alkyl, substituted or unsubstituted aryl, —$OR_{38}$, —$NR_{39}R_{40}$ or —$SR_4$, $R_{36}$ and $R_{37}$ are independently selected from alkoxy, haloalkoxy, thioalkoxy and halothioalkoxy;

$R_{38}$ and $R_{41}$ are independently selected from substituted or unsubstituted alkyl and substituted or unsubstituted aryl;

$R_{39}$ and $R_{40}$ are independently selected from hydrogen, substituted or unsubstituted alkyl and substituted or unsubstituted aryl; or $R_{39}$ and $R_{40}$ may form together a divalent alkylene radical which may be interrupted by one or more heteroatoms;

m, n, q, r, and t independently represent zero, one or two;

M is C-halo, C—$CH_3$, C—$CH_2F$, C—$CH_2Cl$, C—$NO_2$, or N;

or a pesticidally acceptable salt thereof; and (b) a pesticidally acceptable carrier.

6. The pesticidal composition according to claim 5, wherein said composition has from about 0.05 to about 95% (by weight) of an arylpyrazole of formula (I).

7. The pesticidal composition according to claim 6, wherein said composition which has from about 0.00005 to about 90% (by weight) of an arylpyrazole of formula (I).

8. A method for the control of pests at a locus comprising applying to said locus a pesticidally effective amount of an arylpyrazole of formula (I):

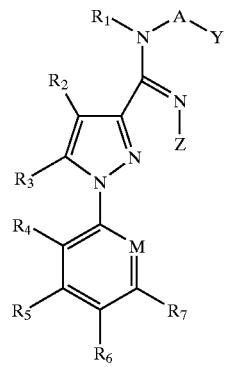

(I)

wherein:

A is —$NR_8$;

Y is hydrogen, substituted or unsubstituted alkyl, substituted or unsubstituted alkenyl, substituted or unsubstituted alkynyl, substituted or unsubstituted aryl, —$S(O)_mR_{10}$, —$P(O)R_{11}R_{12}$, —$P(S)R_{12}$, —$Si(R_{13})(R_{14})(R_{15})$, —$C(O)R_9$, —$C(S)R_9$, cyano or nitro;

$R_1$ is substituted or unsubstituted alkyl or substituted or unsubstituted aryl;

$R_2$ is —$S(O)_nR_{16}$;

$R_3$ is —$NR_{22}R_{23}$;

$R_4$, $R_5$ and $R_7$ are independently selected from hydrogen, halogen and alkyl;

$R_6$ is halogen, haloalkyl, haloalkoxy, —$S(O)_qR_{24}$ or $SF_5$;

$R_8$ is hydrogen or substituted or unsubstituted alkyl;

$R_9$ is hydrogen, substituted or unsubstituted alkyl of $C_1$ to $C_{20}$, substituted or unsubstituted aryl, —$OR_{25}$, —$NR_{26}R_{27}$, or —$SR_{28}$;

$R_{10}$ is substituted or unsubstituted alkyl or substituted or unsubstituted aryl;

$R_{11}$ and $R_{12}$ are independently selected from alkoxy and thioalkoxy;

$R_{13}$, $R_{14}$ and $R_{15}$ are independently selected from alkyl, haloalkyl and aryl;

$R_{16}$ is alkyl, alkenyl, alkynyl, or $C_3$–$C_6$ cycloalkyl, each of which is substituted or unsubstituted by one or more halogen;

$R_{22}$ and $R_{23}$ are independently selected from hydrogen, $NH_2$, —$S(O)_rR_{29}$, —$C(O)R_{30}$, substituted or unsubstituted alkyl, substituted or unsubstituted alkenyl and substituted or unsubstituted alkynyl; or $R_{22}$ and $R_{23}$ may form together a divalent alkylene radical which may be interrupted by one or more heteroatoms;

$R_{24}$ is haloalkyl;

$R_{25}$ and $R_{28}$ are independently selected from substituted or unsubstituted alkyl and substituted or unsubstituted aryl;

$R_{26}$ and $R_{27}$ are independently selected from hydrogen, substituted or unsubstituted alkyl and substituted or unsubstituted aryl; or $R_{26}$ and $R_{27}$ may together form a divalent alkylene radical which may be interrupted by one or more heteroatoms;

$R_{29}$ is substituted or unsubstituted alkyl;

$R_{30}$ is hydrogen, alkyl, haloalkyl, aryl, alkenyl, —$OR_{31}$, —$SR_{31}$, or —$NR_{32}R_{33}$;

$R_{31}$ is alkyl or haloalkyl;

$R_{32}$ and $R_{33}$ are independently selected from hydrogen, alkyl, haloalkyl and aryl;

Z is hydrogen, substituted or unsubstituted alkyl, —$S(O)_rR_{34}$, —$C(O)R_{35}$, —$P(O)R_{36}R_{37}$, —$P(S)R_{36}R_{37}$, cyano or nitro:

$R_{34}$ is substituted or unsubstituted alkyl or substituted or unsubstituted aryl;

$R_{35}$ is hydrogen, substituted or unsubstituted alkyl, substituted or unsubstituted aryl, —$OR_{38}$, —$NR_{39}R_{40}$ or —$SR_{41}$;

$R_{36}$ and $R_{37}$ are independently selected from alkoxy, haloalkoxy, thioalkoxy and halothioalkoxy;

$R_{38}$ and $R_{41}$ are independently selected from substituted or unsubstituted alkyl and substituted or unsubstituted aryl;

$R_{39}$ and $R_{40}$ are independently selected from hydrogen, substituted or unsubstituted alkyl and substituted or unsubstituted aryl; or $R_{39}$ and $R_{40}$ may together form a divalent alkylene radical which may be interrupted by one or more heteroatoms;

m, n, q, r, and t independently represent zero, one or two;

M is C—halo, C—$CH_3$, C—$CH_2F$, C—$CH_2Cl$, C—$NO_2$, or N;

or a pesticidally acceptable salt thereof.

9. The method according to claim 8, wherein the pests are insects.

10. The method according to claim 9, wherein the insects are sucking insects.

11. The method according to claim 8, wherein the locus is a crop area.

12. The method according to claim 8, wherein the arylpyrazole of formula (I) is applied at a locus at a rate of from about 5 g/ha to about 1 kg/ha.

13. The method according to claim 8, wherein said locus is an animal.

14. The method according to claim 13, wherein said compound is applied to said locus at a rate of from about 0.1 to about 20 mg per kg body weight of the animal per day.

15. A process for preparing an arylpyrazole of formula (I) according to claim 1, which comprises (a) when A, Y, $R_2$, $R_3$, $R_4$, $R_5$, $R_6$, $R_7$, and M are defined as in claim 7 and Z is H, reacting a compound of formula (III):

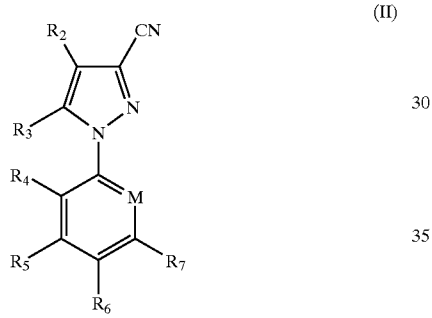

(II)

with a compound of formula (III):

(III)

in which Y and A are defined above; or (b) when A, Y, $R_2$, $R_3$, $R_4$, $R_5$, $R_6$, $R_7$, and M are defined as in claim 17 and Z is H, reacting a compound of formula (IV):

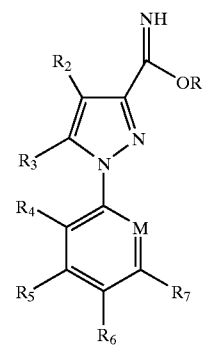

(IV)

wherein R represents alkyl, with a compound of formula (III);

(c) when A, Z, $R_1$, $R_2$, $R_3$, $R_4$, $R_5$, $R_6$, $R_7$, and M are defined as in claim 17 and (I) wherein Y is —$S(O)_mR_{10}$, —$P(O)R_{11}R_{12}$, —$P(S)R_{11}R_{12}$, —$Si(R_{13})(R_{14})(R_{15})$, —$C(O)R_9$, —$C(S)R_9$, cyano, or nitro, reacting of a compound of formula (I) wherein Y is hydrogen, with a sulfenylating, sulftylating, sulfonating, phosphorylating, thiophosphorylating, silylating, acylating, thioacylating, cyanating, or nitrating reagent;

(d) when A, Y, $R_1$, $R_2$, $R_3$, $R_4$, $R_5$, $R_6$, $R_7$, and M are defined as in claim 17 and (1) wherein Z is substituted or unsubstituted alkyl, —$S(O)_rR_{34}$, —$C(O)R_{35}$, —$P(O)R_{36}R_{37}$, —$P(S)R_{36}R_{37}$, cyano or nitro:

(i) reacting a compound of formula (IV) with an alkylating, sulfenylating, sulfinylating, sulfonating, phosphorylating, thiophosphonylating, acylating, cyanating or nitrating reagent, optionally in the presence of a base, and optionally in a solvent at a temperature ranging from approximately −100 to 100° C.; and then (ii) reacting the resulting product with a compound of formula (III); or (e) when A, Y, Z, $R_1$, $R_2$, $R_3$, $R_4$, $R_5$, $R_6$, $R_7$, and M are defined as in claim 17 and in which m, n, q, and r are 1 or 2, oxidizing the corresponding compound in which m, n, q, and r are 0 or 1.

* * * * *